United States Patent [19]
Van Driel

[11] Patent Number: 5,919,153
[45] Date of Patent: Jul. 6, 1999

[54] HARDSHELL VENOUS RESERVOIR WITH ROTATABLE CARDIOTOMY SECTION

[75] Inventor: Michael R. Van Driel, Fountain Valley, Calif.

[73] Assignee: Medtronic, Inc., Minneapolis, Minn.

[21] Appl. No.: 08/728,877

[22] Filed: Oct. 10, 1996

[51] Int. Cl.6 .................................................. A61M 35/00
[52] U.S. Cl. .......................... 604/4; 422/46; 210/321.74
[58] Field of Search ..................... 604/4–6, 410; 422/46, 44, 45, 47, 48; 210/321.74, 321.6, 321.8

[56] References Cited

U.S. PATENT DOCUMENTS

| | | | |
|---|---|---|---|
| 4,876,066 | 10/1989 | Bringham et al. | 422/46 |
| 5,124,127 | 6/1992 | Jones et al. | 422/46 |
| 5,266,265 | 11/1993 | Raible | 422/46 |
| 5,304,164 | 4/1994 | Lindsay | 604/403 |
| 5,411,705 | 5/1995 | Thor et al. | 422/45 |

Primary Examiner—Robert A. Clarke
Assistant Examiner—Ki Yong O
Attorney, Agent, or Firm—Harry G. Weissenberger

[57] ABSTRACT

The cardiotomy inlet connectors of a hardshell venous reservoir are mounted on a turret which is rotatable about the vertical axis of the cover and is in communication with the cardiotomy filter defoamer chamber. The venous inlet connector in turn is mounted on the turret for rotation about the axis of the turret. An axial extension of the venous inlet connector fits sealingly into a venous duct which extends along the axis of the cardiotomy chamber.

9 Claims, 4 Drawing Sheets

5,919,153

HARDSHELL VENOUS RESERVOIR WITH ROTATABLE CARDIOTOMY SECTION

FIELD OF THE INVENTION

This invention relates to venous reservoirs used in cardiac surgery, and more particularly to a hardshell venous reservoir whose cardiotomy inlet connectors, venous inlet connector and cover are rotatably positionable at any desired horizontal angle to each other, and in which the cardiotomy inlet connectors discharge directly into the cardiotomy filter/defoamer.

BACKGROUND OF THE INVENTION

In cardiac surgery, the patient's blood is heavily diluted with saline solution to reduce its viscosity and improve the manageability of the cardiopulmonary bypass circuit. The resulting extra volume of diluted blood is stored in a venous reservoir interposed between the vena cava tap and the pump of the heart-lung machine, which pumps the blood through an oxygenator and back into the patient's aorta. The venous reservoir also serves as a fluid buffer in the external circulation system to smooth out variations between the blood flow available from the vena cava and the demands of the heart-lung machine pump.

Because a substantial amount of blood escapes into the patient's chest cavity during the surgery, it is necessary to recover this cardiotomy blood with a suction device, filter it, defoam it, and then return it to the external circulation system. Although cardiotomy blood filtering and defoaming was originally done in a hardshell cardiotomy reservoir separate from the then collapsible venous reservoir, it has become conventional in recent years to combine the cardiotomy reservoir and the venous reservoir into a single hardshell venous reservoir.

A representative type of conventional hardshell venous reservoir has two distinct fluid paths: a venous blood path which enters the reservoir through a centrally located venous intake in the cover of the reservoir, and is conveyed into a defoaming chamber in which any air bubbles present in the venous blood are removed before the venous blood is discharged into the body of the reservoir.

The cardiotomy blood enters the reservoir through a plurality of cardiotomy inlet connectors in the cover of the reservoir (typically, three or four separate cardiotomy suction devices are used during cardiac surgery) and is conveyed into a much more elaborate filtering/defoaming chamber where cellular and surgical debris and large amounts of air are removed from the cardiotomy blood.

In use, the reservoir is typically so positioned as to be close to the patient, with the venous inlet connector turned toward the patient to minimize the length of the relatively large line from the vena cava. The suction pumps for the cardiotomy circuit may, however, be placed most anywhere with respect to the reservoir; usually away from the patient or off to one side.

In prior art reservoirs, the cardiotomy inlet connectors were fixed or were swivelable through only a limited arc with respect to the venous blood intake. In the latter case, the cardiotomy blood from the inlet connectors was passed through a swivelable common conduit before entering the filter/defoamer chamber. Failure of that common conduit during swiveling would shut down the entire cardiotomy circuit.

The limited mobility of prior art connectors posed a problem for the perfusionist: having to bring a plurality of lines around the cover manifold of the reservoir, particularly when moving equipment during surgery, not only resulted in a maze of criss-crossing lines (a number of other lines are also attached to the reservoir cover for monitoring and other purposes), but subjected the lines to kinking under the weight of the blood.

SUMMARY OF THE INVENTION

The present invention solves the above-described problem by mounting the cardiotomy inlet connectors and venous inlet connector in a rotatable turret which allows them to be freely rotated with respect to each other, even during surgery, so as to face in any desired direction with respect to the reservoir and to any other connectors mounted on the reservoir cover. Also, the turret of this invention allows cardiotomy blood to be directly and unobstructedly discharged into the cardiotomy filtering/defoaming chamber without first going through a common conduit.

DESCRIPTION OF THE PREFERRED EMBODIMENT

Figure 1:
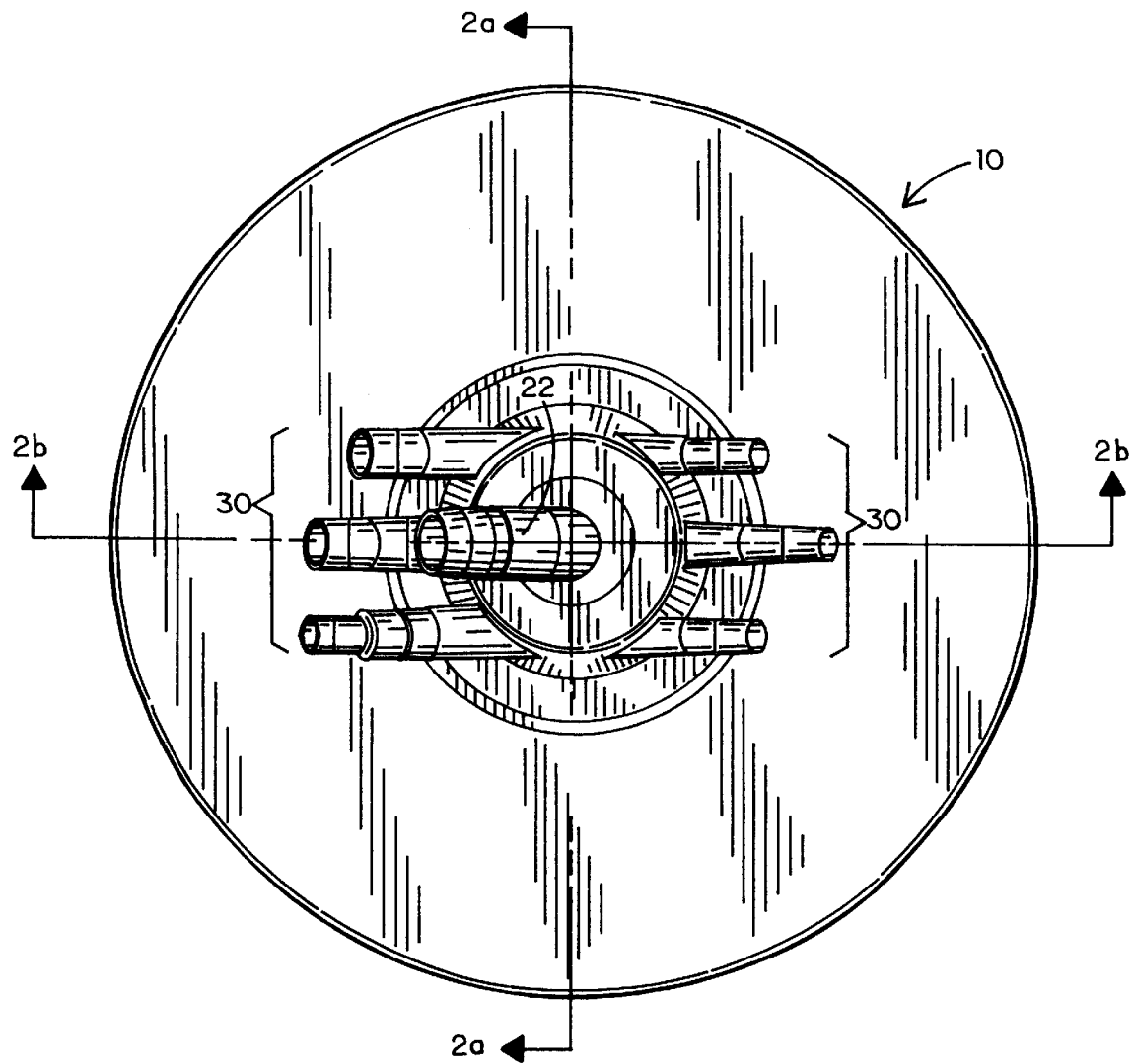
FIG. 1 is a plan view of a venous reservoir using the turret of this invention.
Figure 2A:
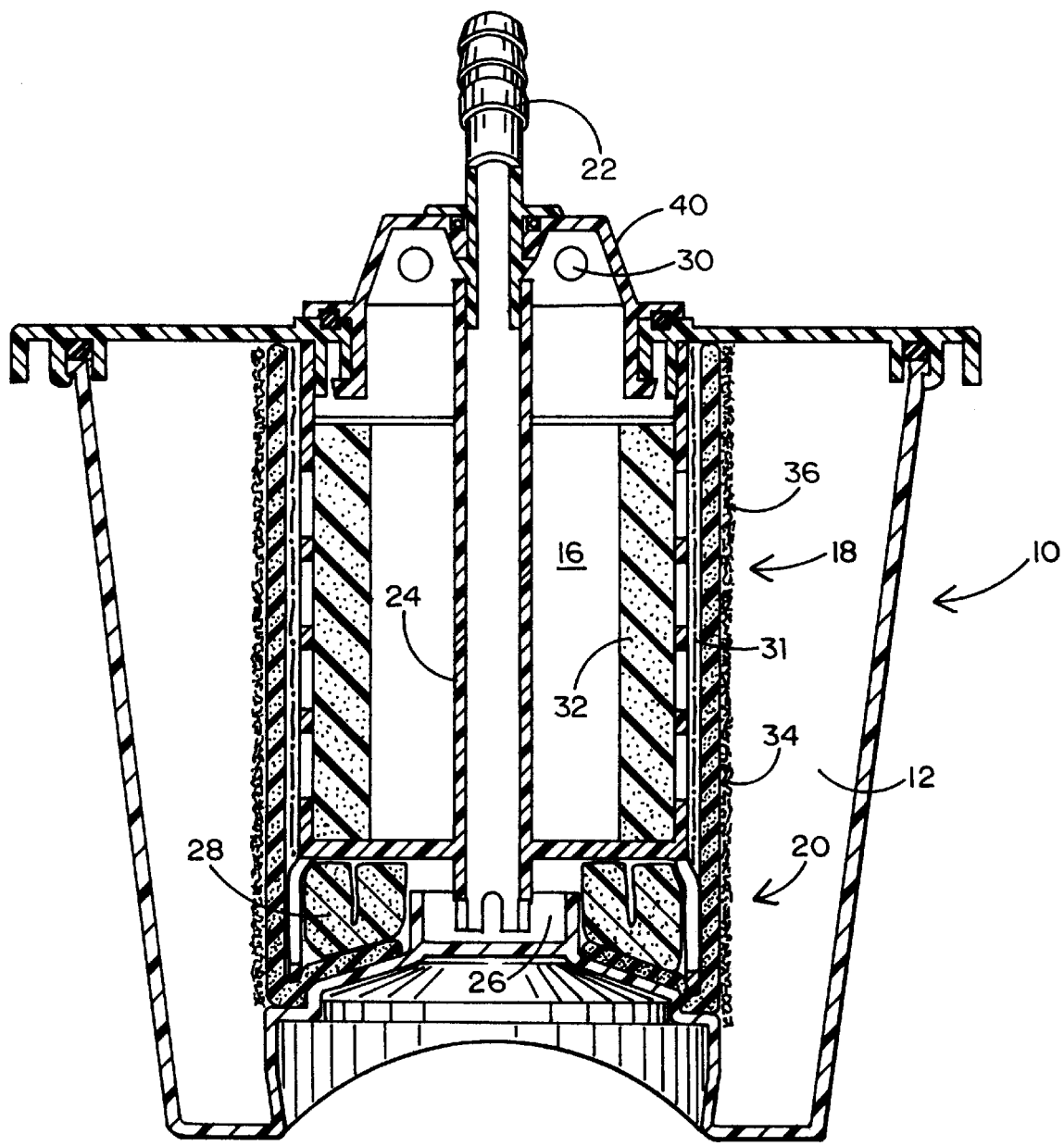
FIGS. 2a and 2b are vertical sections of the reservoir of FIG. 1 along lines A—A and B—B of FIG. 1, respectively.
Figure 2B:
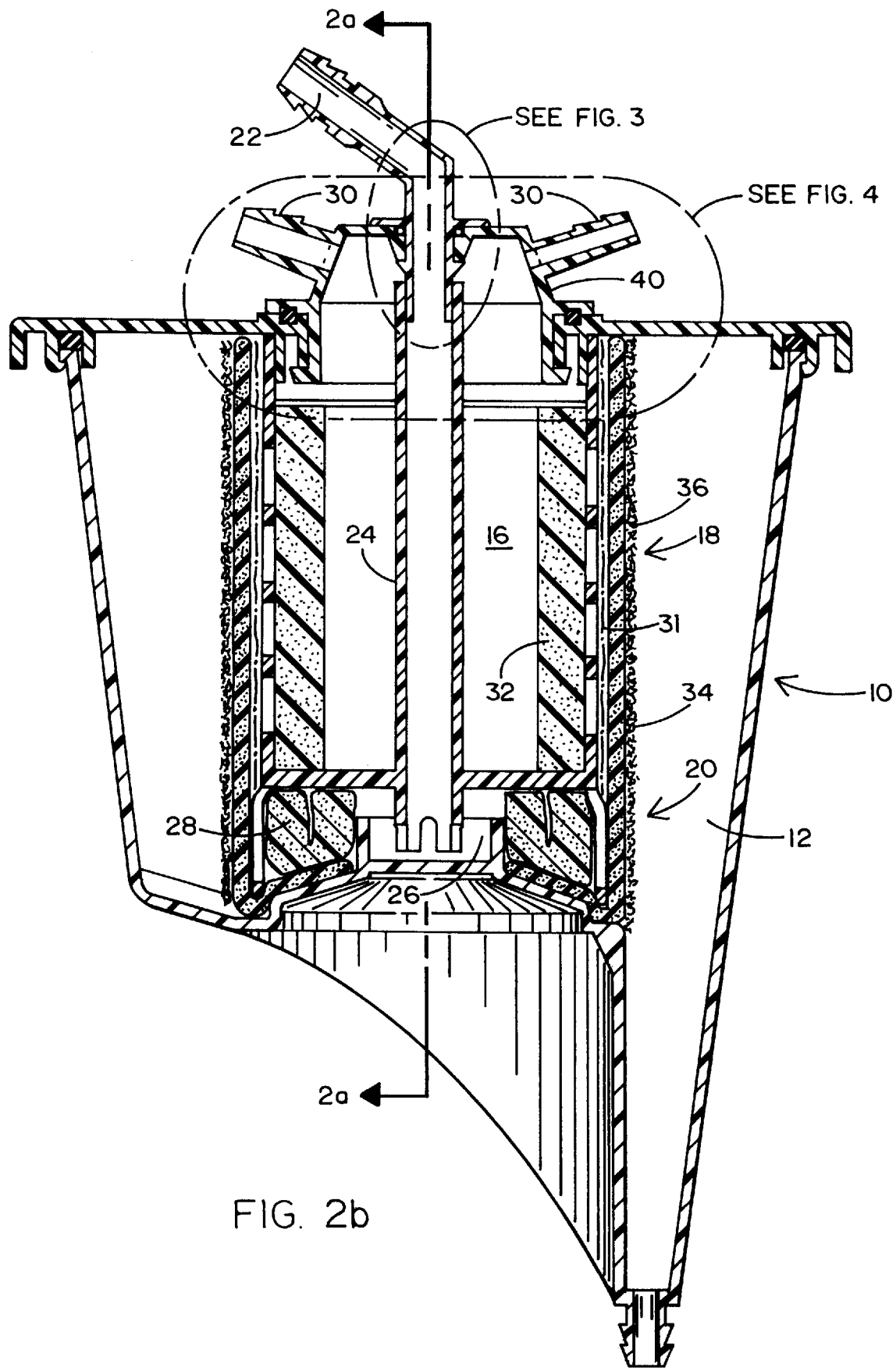
Figure 3:
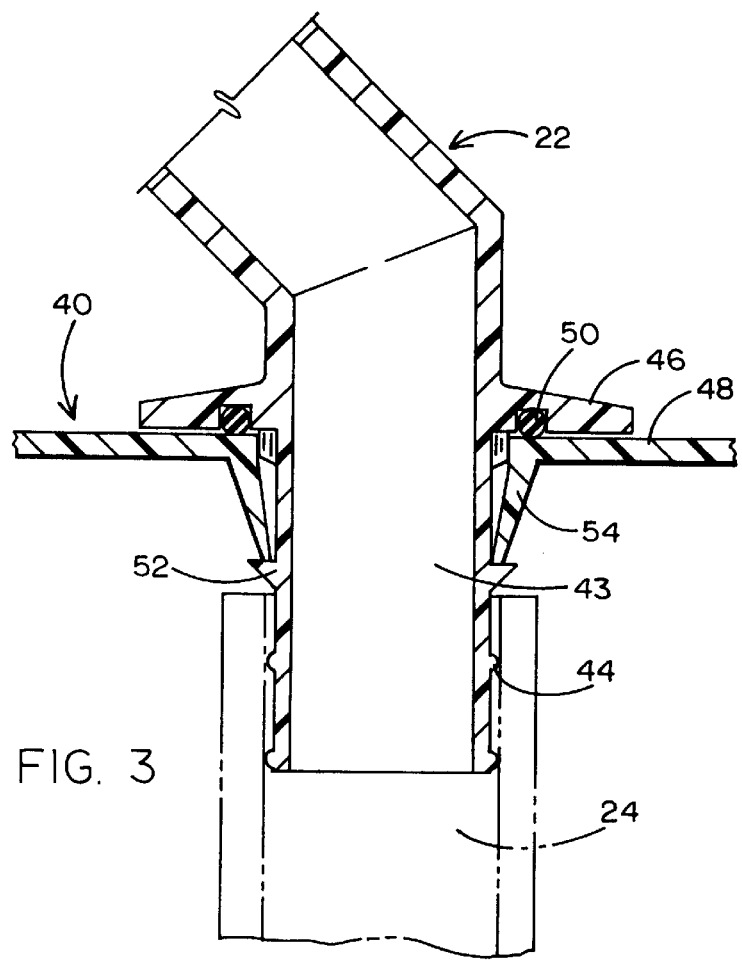
FIG. 3 is an enlarged cross section of the area 3—3 of FIG. 2b.
Figure 4:
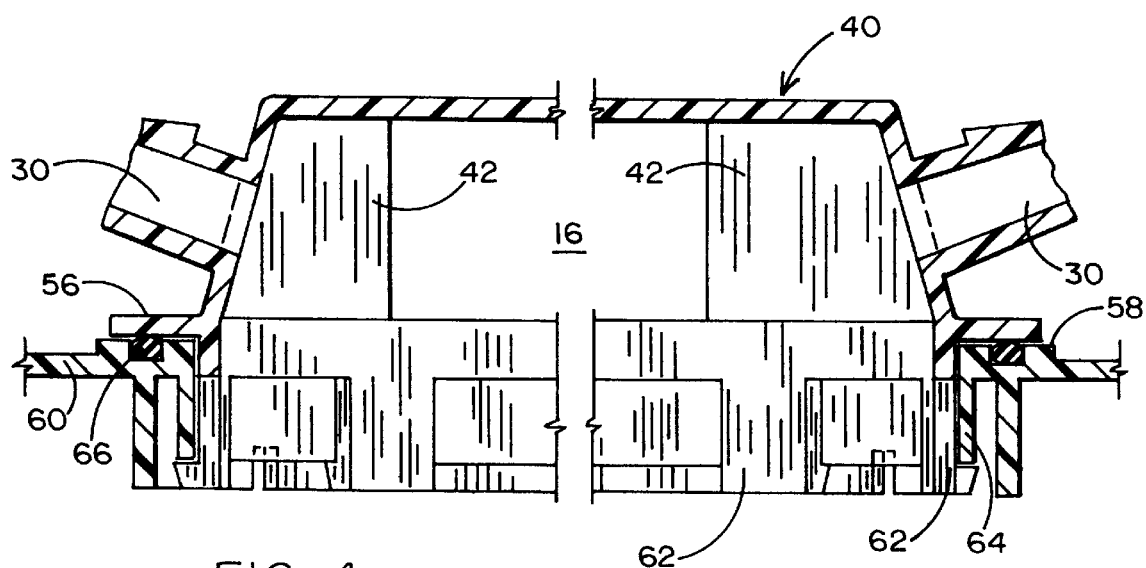
FIG. 4 is an enlarged cross section of the area 4—4 of FIG. 2b.

FIGS. 1 and 2 depict the hardshell venous reservoir 10 of this invention. The reservoir 10 conventionally includes a body 12 in which defoamed filtered blood is stored until it is pumped out through the outlet connector 14; a cardiotomy chamber 16 for receiving cardiotomy blood; a cardiotomy/defoaming filter 18 for filtering and defoaming cardiotomy blood before releasing it into the body 12; and a venous blood defoamer 20 which removes any microair in the venous blood.

The main flow of essentially clean venous blood enters the reservoir 10 through a venous inlet connector 22 disposed at an angle to the axis of the reservoir 10, and ascends through the flow tube 24 into the venous chamber 26. From there it flows through the venous defoamer 28 directly into the body 12.

The secondary flow of cell debris-laden, foamy blood from the cardiotomy suckers, which suction blood escaping into the surgical field, enters the reservoir 10 through several cardiotomy connectors 30 which discharge it into the cardiotomy chamber 16. From there the cardiotomy blood flows through the filter/defoamer 18 which may be of conventional design. Typically, the filter/defoamer 18 may consist of a filter layer 31 sandwiched between two defoamer layers 32, 34 and encased in a sock 36, all of which are well known in the art.

In order to allow the perfusionist to set up his or her equipment with a minimum of bends or crossings in the tubing, it is highly desirable to be able to change at will the orientation of the venous inlet connector 22 and of the cardiotomy connectors 30 with respect to each other and with respect to the reservoir body 12. The situation is further complicated by the fact that some perfusionists like to use smaller (e.g. 7 mm) cardiotomy connectors, while others prefer larger (e.g. 10 mm) connectors. Therefore, two sets of connectors are typically provided, facing in opposite directions from each other.

The invention gives perfusionists a wide choice by mounting the cardiotomy connectors 30 on a turret 40 which can be rotated through 360° with respect to the body 10. All the cardiotomy connectors 30 discharge blood directly into the cardiotomy chamber 16 and are separated from each other by baffles 42 in the chamber 16 to prevent backflow through unused connectors 30.

The venous inlet connector 22 is itself mounted on the turret 40 for 360° rotation with respect to the turret 40. The venous inlet connector 22 discharges blood into the flow tube 24 through an integral axially extending rotatable shank 43 ending in a sliding fitting 44 which provides a rotatable seal between the connector 22 and the tube 24.

The shank 43 has a wide flange 46 which rides on the top surface 48 of turret 40 and provides stability to the connector 22. A resilient O-ring 50 is interposed between the flange 46 and the surface 48 to bias a ridge 52 on shank 43 against resilient snaps 54 which hold shank 43 in turret 40.

The turret 40 also has a radially extending flange 56 which rides on the surface 58 of the cover 60 of reservoir 12. The turret 40 also carries a plurality of resilient fingers 62 which hold the turret 40 in the cover 60 by engaging an annular flange 64 depending from the cover 60 around the periphery of the cardiotomy chamber 16. A fabricated O-ring 65 is interposed between the flange 56 of the turret 40 and the surface 58 to bias the fingers 62 into firm engagement with the flange 64 of the cover 60.

In addition to their biasing action, the O-rings 50 and 66 also provide airtight seals in any position, and even during rotation, between the venous inlet connector 22 and the turret 40, and between the turret 40 and the cover 60 while allowing unrestricted rotational positioning of the connector 22, cardiotomy turret 40, and cover 60 relative to each other.

It is understood that the exemplary hardshell venous reservoir with rotatable cardiotomy section described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

I claim:
1. A venous blood reservoir, comprising:
   a) a body for storing blood;
   b) a cardiotomy chamber;
   c) a filter-defoamer arranged to filter and defoam blood flowing from said cardiotomy chamber into said body;
   d) a substantially horizontal cover covering said body;
   e) a venous duct axially extending substantially vertically from said cover into said body for conveying venous blood into said body;
   f) a venous inlet connector in blood-conveying relation to said venous duct; and
   g) a set of cardiotomy inlet connectors in blood-conveying communication with said cardiotomy chamber;
   h) said set of cardiotomy inlet connectors and said venous inlet connector being unrestrictedly rotatable with respect to said cover and each other about a common axis perpendicular to the plane of said cover.

2. The reservoir of claim 1, in which said cardiotomy inlet connectors are individually and separately in direct communication with said cardiotomy chamber.

3. The reservoir of claim 1, further comprising:
   i) a turret positioned on said cover to close off said cardiotomy chamber, said turret being rotatable with respect to said cover, said cardiotomy inlet connectors being mounted on said turret.

4. The reservoir of claim 3, in which pluralities of cardiotomy inlet connectors are mounted on opposite sides of said turret.

5. The reservoir of claim 3, further comprising:
   j) a venous inlet connector mounted centrally of said turret for rotation with respect to said turret about the axis of said turret.

6. The reservoir of claim 5, in which said venous inlet connector has a portion extending axially of said turret and duct, said portion being insertable into said duct and, when so inserted, forming therewith a sealed venous blood path.

7. The reservoir of claim 6, in which said portion is arranged to be sealingly rotatably snap-locked to said turret.

8. The reservoir of claim 3, in which said turret sealingly engages said cover when positioned thereon.

9. The reservoir of claim 8, in which said turret is arranged to be sealingly rotatably snap-locked to said turret.

* * * * *